United States Patent
Nakamura et al.

(10) Patent No.: US 11,141,710 B2
(45) Date of Patent: Oct. 12, 2021

(54) ENDOTOXIN ADSORBENT

(71) Applicant: NAGASE CHEMTEX CORPORATION, Osaka (JP)

(72) Inventors: Daisuke Nakamura, Hyogo (JP); Yuki Maeda, Hyogo (JP)

(73) Assignee: NAGASE CHEMTEX CORPORATION, Osaka (JP)

( * ) Notice: Subject to any disclaimer, the term of this patent is extended or adjusted under 35 U.S.C. 154(b) by 89 days.

(21) Appl. No.: 16/479,358

(22) PCT Filed: Jan. 22, 2018

(86) PCT No.: PCT/JP2018/001838
§ 371 (c)(1),
(2) Date: Jul. 19, 2019

(87) PCT Pub. No.: WO2018/139415
PCT Pub. Date: Aug. 2, 2018

(65) Prior Publication Data
US 2019/0351389 A1 Nov. 21, 2019

(30) Foreign Application Priority Data

Jan. 25, 2017 (JP) .............................. JP2017-010966

(51) Int. Cl.
*B01J 20/22* (2006.01)
*B01D 15/22* (2006.01)
*B01J 41/16* (2006.01)

(52) U.S. Cl.
CPC .............. *B01J 20/22* (2013.01); *B01D 15/22* (2013.01); *B01J 41/16* (2013.01)

(58) Field of Classification Search
CPC ............ B01J 20/22; B01J 41/16; B01D 15/22
USPC ....................................................... 502/402
See application file for complete search history.

(56) References Cited

U.S. PATENT DOCUMENTS

| | | | |
|---|---|---|---|
| 4,791,063 A | 12/1988 | Hou et al. | |
| 2002/0130082 A1 | 9/2002 | Todokoro et al. | |
| 2007/0213258 A1 | 9/2007 | Nakayama et al. | |
| 2018/0178192 A1 | 6/2018 | Sakata et al. | |

FOREIGN PATENT DOCUMENTS

| | | |
|---|---|---|
| JP | 2002-155103 | 5/2002 |
| JP | 2002-263486 | 9/2002 |
| JP | 2002-355553 | 12/2002 |
| JP | 2009-13204 | 1/2009 |
| JP | 2009-173678 | 8/2009 |
| WO | 2017/018524 | 2/2017 |

OTHER PUBLICATIONS

International Search Report, dated Mar. 27, 2018 in corresponding International Patent Application No. PCT/JP2018/001838.
Partial Supplementary European Search Report dated Jan. 7, 2020 in corresponding European Patent Application No. 18744832.9.
Morimoto S. et al., "Preparations and Applications of Polyethyleneimine-Immobilized Cellulose Fibers for Endotoxin Removal" Polymer Journal, 1995, vol. 27, No. 8, pp. 831-839.

*Primary Examiner* — Edward M Johnson
(74) *Attorney, Agent, or Firm* — Wenderoth, Lind & Ponack, L.L.P.

(57) ABSTRACT

An endotoxin adsorbent comprising a crystalline cellulose having a nitrogen atom-containing cationic group can sufficiently remove endotoxin from a material containing endotoxin to be removed and containing a substance having a cationic group and can efficiently remove endotoxin also from a highly viscous material. The nitrogen atom-containing cationic group may be typically a functional group derived from a polyvalent amine and/or a quaternary ammonium salt. The crystalline cellulose having a nitrogen atom-containing cationic group may comprise the nitrogen atom-containing cationic group at a content of 0.05 to 3 meq/dry·g in terms of anion exchange capacity.

13 Claims, No Drawings

ENDOTOXIN ADSORBENT

TECHNICAL FIELD

The present invention relates to an endotoxin adsorbent and an endotoxin removal method using the adsorbent.

BACKGROUND ART

Endotoxin (ET) (hereinafter also called "ET") is a toxic substance and specifically refers to lipopolysaccharide (LPS) that is a component of an outer membrane of gram-negative bacteria. ET is composed of a polysaccharide and lipid A, and the lipid A is mainly responsible for its toxicity. ET causes fever or shock reaction when taken into a living body due to ET contamination of an injectable solution or the like. Hence, the Japanese Pharmacopoeia defines the ET concentration in injectable solutions as being 10 to 100 pg/ml (0.1 to 1.0 endotoxin unit (EU)/ml). In recent years, for example, isolation and purification of DNA from recombinant *Escherichia coli* or the like has been studies for use as a DNA vaccine. The DNA thus obtained, however, contains residual ET derived from bacterial cells. In order to administer the thus-obtained DNA as a DNA vaccine to a living body, the residual ET needs to be removed. There is accordingly a strong desire to develop a method for removing ET from pharmaceutical products. In addition, foods should not contain ET, and there is another desire to remove ET from processed food materials.

A well-known exemplary method for removing ET uses various ET adsorbents. For example, Patent Literature 1 discloses an ET adsorbent comprising a basic substance bonded thereto through a crosslinking agent and having a molecular weight exclusion limit of 6,000 or less, specifically, an ET adsorbent comprising a spherical cellulose to which poly($\varepsilon$-L-lysine) is immobilized, and teaches that the ET adsorbent can selectively adsorb ET from an aqueous solution containing proteins at high concentrations.

The ET adsorbent disclosed in Patent Literature 1, however, cannot sufficiently remove ET when a material containing ET to be removed contains a substance having a cationic group such as an amino group, especially when the whole molecule thereof has a cationic charge, due to competitive ET adsorption between the cationic group-containing substance and the ET adsorbent bonded to a basic substance.

When the material containing ET to be removed is an aqueous composition, the ET adsorbent preferably has a hydrophilic base material in order to facilitate the contact between the material containing ET to be removed and the ET adsorbent. As the hydrophilic base material, a hydrophilic polymer compound is easy to use. Commonly, when an ET adsorbent comprises a hydrophilic polymer compound as the base material, the base material strongly interacts with water molecules. Hence, when used in a batch system, the adsorbent has poor filterability, whereas when used in a column system, the adsorbent needs high pressure for allowing a liquid to pass. Such an adsorbent thus has poor operating efficiency, and this causes serious problems especially when ET is removed from a viscous solution.

In view of these circumstances, there is a strong demand for ET adsorbents applicable to a wider range of materials containing ET to be removed, specifically in the pharmaceutical and food fields.

CITATION LIST

Patent Literature

Patent Literature 1: JP 2002-263486 A

SUMMARY OF INVENTION

Technical Problem

The present invention has a main object to provide an ET adsorbent capable of sufficiently removing ET from a material containing ET to be removed and containing a substance having a cationic group and capable of efficiently removing ET from viscous materials.

Solution to Problem

The inventors of the present invention have carried out intensive studies in order to attain the above object and have found that a crystalline cellulose having a nitrogen atom-containing cationic group can efficiently remove ET from a material containing a substance having a cationic group. The inventors of the present invention have also found that the crystalline cellulose having a nitrogen atom-containing cationic group enables rapid filtration in a batch system even when the crystalline cellulose is applied to a viscous material. The inventors of the present invention have further found that the crystalline cellulose having a nitrogen atom-containing cationic group can allow a liquid to pass immediately without pressure on a column and can remove ET from a viscous material in a column system.

The present invention has been completed on the basis of the above findings and provides the following aspects [1] to [25].

[1] An endotoxin adsorbent comprising a crystalline cellulose having a nitrogen atom-containing cationic group.

[2] The endotoxin adsorbent according to [1], wherein the nitrogen atom-containing cationic group is a functional group derived from a polyvalent amine and/or a quaternary ammonium group.

[3] The endotoxin adsorbent according to [1] or [2], wherein the crystalline cellulose having a nitrogen atom-containing cationic group comprises the nitrogen atom-containing cationic group at a content of 0.05 to 3 meq/dry·g in terms of anion exchange capacity.

[4] A column for removing endotoxin, the column comprising the endotoxin adsorbent according to any one of [1] to [3] therein.

[5] A method of removing endotoxin, the method comprising a step of bringing the endotoxin adsorbent according to any one of [1] to [3] into contact with a material containing endotoxin to be removed.

[6] A method of producing a material from which endotoxin has been removed, the method comprising a step of bringing the endotoxin adsorbent according to any one of [1] to [3] into contact with a material containing endotoxin to be removed.

[7] A method of using a crystalline cellulose having a nitrogen atom-containing cationic group as an endotoxin adsorbent.

[8] The method according to [7], wherein the nitrogen atom-containing cationic group is a functional group derived from a polyvalent amine and/or a quaternary ammonium group.

[9] The method according to [7] or [8], wherein the crystalline cellulose having a nitrogen atom-containing cationic group comprises the nitrogen atom-containing cationic group at a content of 0.05 to 3 meq/dry·g in terms of anion exchange capacity.

[10] A method of using a column comprising a crystalline cellulose having a nitrogen atom-containing cationic group therein as a column for removing endotoxin.

[11] The method according to [10], wherein the nitrogen atom-containing cationic group is a functional group derived from a polyvalent amine and/or a quaternary ammonium group.

[12] The method according to [10] or [11], wherein the crystalline cellulose having a nitrogen atom-containing cationic group comprises the nitrogen atom-containing cationic group at a content of 0.05 to 3 meq/dry·g in terms of anion exchange capacity.

[13] A method of removing endotoxin, the method comprising a step of bringing a crystalline cellulose having a nitrogen atom-containing cationic group into contact with a material containing endotoxin to be removed.

[14] The method according to [13], wherein the nitrogen atom-containing cationic group is a functional group derived from a polyvalent amine and/or a quaternary ammonium group.

[15] The method according to [13] or [14], wherein the crystalline cellulose having a nitrogen atom-containing cationic group comprises the nitrogen atom-containing cationic group at a content of 0.05 to 3 meq/dry·g in terms of anion exchange capacity.

[16] A method of producing a material from which endotoxin has been removed, the method comprising a step of bringing a crystalline cellulose having a nitrogen atom-containing cationic group into contact with a material containing endotoxin to be removed.

[17] The method according to [16], wherein the nitrogen atom-containing cationic group is a functional group derived from a polyvalent amine and/or a quaternary ammonium group.

[18] The method according to [16] or [17], wherein the crystalline cellulose having a nitrogen atom-containing cationic group comprises the nitrogen atom-containing cationic group at a content of 0.05 to 3 meq/dry·g in terms of anion exchange capacity.

[19] Use of a crystalline cellulose having a nitrogen atom-containing cationic group as an endotoxin adsorbent.

[20] The use according to [19], wherein the nitrogen atom-containing cationic group is a functional group derived from a polyvalent amine and/or a quaternary ammonium group.

[21] The use according to [19] or [20], wherein the crystalline cellulose having a nitrogen atom-containing cationic group comprises the nitrogen atom-containing cationic group at a content of 0.05 to 3 meq/dry·g in terms of anion exchange capacity.

[22] Use of a column comprising a crystalline cellulose having a nitrogen atom-containing cationic group therein as a column for removing endotoxin.

[23] The use according to [22], wherein the nitrogen atom-containing cationic group is a functional group derived from a polyvalent amine and/or a quaternary ammonium group.

[24] The use according to [22] or [23], wherein the crystalline cellulose having a nitrogen atom-containing cationic group comprises the nitrogen atom-containing cationic group at a content of 0.05 to 3 meq/dry·g in terms of anion exchange capacity.

[25] A glucan, a collagen, or a solution thereof comprising endotoxin at a content of 20 EU/g or less.

Advantageous Effects of Invention

ET as a lipopolysaccharide has an anionic heterosaccharide such as N-acetylgalactosamine and N-acetylglucosamine or a hydrogenphosphate ion as an anion. Hence, use of an ET adsorbent having a cationic group for removal of ET from a material containing a substance having a cationic group generally causes competitive ET adsorption between the ET adsorbent and the substance having a cationic group, resulting in insufficient ET removal. In contrast, the ET adsorbent of the present invention has a cationic group but can sufficiently remove ET from a material containing a substance having a cationic group.

The ET adsorbent of the present invention comprises a highly hydrophilic crystalline cellulose as a base material, thus is compatible with an aqueous composition, and consequently can efficiently remove ET from an aqueous material containing ET to be removed. Typically, with an ET adsorbent comprising a hydrophilic polymer compound as the base material, the base material strongly interacts with water molecules. Hence, when used in a batch system, the adsorbent has poor filterability, and when used in a column system, the adsorbent needs high pressure for allowing a liquid to pass.

In contrast, the ET adsorbent of the present invention comprises a hydrophilic base material, but after mixture with an aqueous material containing ET to be removed, the adsorbent is readily separated from the aqueous material. Hence, after contact in a batch system with a material containing ET to be removed, the material from which the ET has been removed can be immediately separated by filtration. When the ET adsorbent of the present invention is packed in a column through which a material containing ET to be removed is allowed to pass, the material can speedily pass without high pressure. Many pharmaceutical products and food materials are highly viscous materials such as polysaccharides, but use of the ET adsorbent of the present invention enables the rapid removal of ET from such a highly viscous material.

When an ET adsorbent has a uniform pore size, some components contained in a material containing ET to be removed are trapped by the pores and are difficult to be recovered. In contrast, the ET adsorbent of the present invention comprises a crystalline cellulose having various sized pores as the base material and thus achieves a satisfactory recovery rate of components contained in a material containing ET to be removed.

The crystalline cellulose has been generally used as a diluent for pharmaceutical or food products and has established safety. Accordingly, the ET adsorbent of the present invention is highly safe and can be suitably used to remove ET from pharmaceutical or food products.

DESCRIPTION OF EMBODIMENTS

The present invention will now be described in detail.

(1) Endotoxin Adsorbent

The endotoxin adsorbent (ET adsorbent) of the present invention is an ET adsorbent comprising a crystalline cellulose having a nitrogen atom-containing cationic group. ET is also called "lipopolysaccharide (LPS)".

Crystalline Cellulose

The "crystalline cellulose" is a cellulose prepared by depolymerization of a cellulose-based substance through, for example, acidic hydrolysis, alkali oxidative decomposition, enzymatic decomposition, and/or steam explosion decomposition and subsequent purification. In other words, the "crystalline cellulose" is prepared by purification of a crystalline portion isolated from a cellulose-based substance. The "crystalline cellulose" is also called "microcrystalline cellulose". The cellulose-based substance is also called pulp.

Examples of the specific method of producing a crystalline cellulose from a cellulose-based substance include a method by hydrolysis with hydrochloric acid, sulfuric acid, or the like and subsequent purification (JP 1994-316535 A), a method by oxidative decomposition with a base such as sodium hydroxide and subsequent purification (Kobunshi Kagaku (Polymer Chemistry), Vol. 29, No. 329, pp. 647-651), and a method by oxidative decomposition with dichromic acid or hypochlorous acid and subsequent purification (Kobunshi Kagaku, Vol. 29, No. 329, pp. 652-656).

The crystalline cellulose may be a commercial product. Examples of the commercially available crystalline cellulose include Comprecel (registered trademark) of Mingtai Chemical Co., Ltd. and CEOLUS (registered trademark) of Asahi Kasei Corporation.

Nitrogen Atom-Containing Cationic Group

The crystalline cellulose used in the present invention has a nitrogen atom-containing cationic group. The crystalline cellulose having a nitrogen atom-containing cationic group may be a crystalline cellulose intrinsically having a nitrogen atom-containing cationic group or a crystalline cellulose to which a nitrogen atom-containing cationic group is introduced.

Examples of the nitrogen atom-containing cationic group include amino groups (such as primary amino groups, secondary amino groups, and tertiary amino groups), quaternary ammonium groups, an imino group, an amidine group, a guanidino group, an imidazole group, a quaternary imidazolium group, a pyridyl group, and a quaternary pyridinium group. The amino group may be any of a functional group formed by elimination of a hydrogen atom from ammonia (—NH$_2$), a functional group formed by elimination of a hydrogen atom from a primary amine (—NHR), and a functional group formed by elimination of a hydrogen atom from a secondary amine (—NRR').

The nitrogen atom-containing cationic group may be acyclic or may be cyclic.

The nitrogen atom-containing cationic group may be introduced, for example, to a hydroxy group of cellulose. Examples of the method of introducing the nitrogen atom-containing cationic group include a method by activation of a hydroxy group of cellulose with an activating agent and subsequent reaction with a cationic compound containing a nitrogen atom. When a nitrogen atom-containing cationic group itself has a reactive group, pretreatment with an activating agent is not necessary.

Examples of the activating agent include epoxy group donors such as chloromethyloxirane (epichlorohydrin), glycidyl methacrylate, glycidyl acrylate, diglycidyl ether, epibromohydrin, and ethylene glycol diglycidyl ether, p-toluenesulfonyl chloride, 2-fluoro-1-methylpyridinium, chloroacetyl chloride, hexamethylene diisocyanate, m-xylene diisocyanate, and toluene-2,4-diisocyanate.

The activating agent is preferably an epoxy group donor and more preferably chloromethyloxirane (epichlorohydrin).

The activating agents may be used singly or in combination of two or more of them.

Examples of the nitrogen atom-containing cationic compound as the donor of the nitrogen atom-containing cationic group include ammonia, amidines, monovalent amines, polyvalent amines, quaternary ammonium salts, quaternary imidazolium salts, and quaternary pyridinium salts.

Examples of the monovalent amine include aliphatic amines especially including alkylamines (primary amines such as methylamine and ethylamine; secondary amines such as dimethylamine and diethylamine; and tertiary amines such as trimethylamine, triethylamine, tripropylamine, tributylamine, and diisopropylethylamine); aromatic amines (including primary amines such as aniline and toluidine); heterocyclic amines (including secondary amines such as pyrrolidine, piperidine, morpholine, and imidazole; and tertiary amines such as pyridine, 2,4,6-trimethylpyridine (collidine), 2,6-lutidine, quinoline, N-methylmorpholine, and N-ethylmorpholine); and alkanolamines and amino alcohols (primary amines such as monomethanolamine, monoethanolamine, monoisopropanolamine, 2-amino-2-methyl-1-propanol, 2-amino-2-methyl-1,3-propanediol, 3-amino-1,2-propanediol, 3-dimethylamino-1,2-propanediol, and tris(hydroxymethylamino)methane; secondary amines such as diethanolamine, diisopropanolamine, N-methylethanolamine, and N-ethylethanolamine; and tertiary amines such as triethanolamine, triisopropanolamine, N-dimethylaminoethanol, and N-diethylaminoethanol).

Examples of the polyvalent amine include aliphatic diamines such as ethylenediamine, tetramethylethylenediamine, tetramethylenediamine, and hexamethylenediamine; alicyclic diamines such as 4,4'-diamino-3,3'-dimethyldicyclohexylmethane, N,N,N',N'-tetramethyl-1,6-diaminohexane, cyclohexanediamine, and isophoronediamine; aromatic diamines such as phenylenediamine, diaminonaphthalene, and xylylenediamine; heterocyclic diamines such as piperazine; trivalent or higher valent aliphatic amines such as diethylenetriamine, triethylenetetramine, tetraethylenepentamine, pentaethylenehexamine, hexaethylenepentamine, tris(2-aminoethyl)amine, tris(3-aminopropyl)amine, and guanidine; and trivalent or higher valent aromatic amines such as melamine.

Examples of the polyvalent amine also include polyethyleneimine, polyvinylamine, polyallylamine, amino acids (specifically basic amino acids such as lysine, arginine, histidine, ornithine, and tryptophan), amino acid polymers (specifically basic amino acid polymers such as polylysine, polyarginine, polyhistidine, polyornithine, and polytryptophan), and polymers having an amino group such as polycreatinine. The polymer may be linear or branched. The polymer may have a number average molecular weight of, for example, 50 or more, 100 or more, or 150 or more and 1,000,000 or less, 100,000 or less, 10,000 or less, 5,000 or less, 2,000 or less, or 1,000 or less. The polymer has a number average molecular weight of, for example, 50 to 1,000,000, 50 to 100,000, 50 to 10,000, 50 to 5,000, 50 to 2,000, 50 to 1,000, 100 to 1,000,000, 100 to 100,000, 100 to 10,000, 100 to 5,000, 100 to 2,000, 100 to 1,000, 150 to 1,000,000, 150 to 100,000, 150 to 10,000, 150 to 5,000, 150 to 2,000, or 150 to 1,000.

Examples of the quaternary ammonium salt having a reactive group include glycidyltrimethylammonium salts (such as a hydrochloride and a hydrobromide). For example, a quaternary amine quaternized by alkylation of the above-exemplified tertiary amine may also be used.

Examples of the quaternary imidazolium salt include 1-decyl-3-methylimidazolium salts, 1-methyl-3-octylimidazolium salts, and 1-methyl-benzoimidazolium salts (such as a hydrochloride and a hydrobromide).

Examples of the quaternary pyridinium salt include butylpyridinium salts and dodecylpyridinium salts (such as a hydrochloride and a hydrobromide).

The nitrogen atom-containing cationic compound is preferably a polyvalent amine, a monovalent amine, or a quaternary ammonium salt, more preferably a polyvalent amine or a quaternary ammonium salt, and even more preferably ethylenediamine, hexamethylenediamine, tetraethylenepentamine, N,N,N',N'-tetramethyl-1,6-diaminohexane, arginine, polyethyleneimine, glycidyltrimethylammonium, or tetramethylethylenediamine.

The nitrogen atom-containing cationic compounds may be used singly or in combination of two or more of them.

When two or more cationic compounds are used, crystalline celluloses to which the corresponding cationic compounds are introduced may be used, or a crystalline cellulose to which two or more cationic compounds are introduced may be used.

After reaction of a crystalline cellulose with a nitrogen atom-containing cationic compound, the product may be further modified to increase the cationic properties. Examples of the compound that quaternizes an amino group in order to increase the cationic properties include chloromethyloxirane (epichlorohydrin), iodomethane, and iodoethane. Examples of the method of additionally introducing a nitrogen atom-containing cationic group to increase the cationic properties include a method by activation of an introduced cationic group with an activating agent and subsequent reaction with a nitrogen atom-containing cationic compound that has a cationic group same as or different from the previously introduced cationic group. As the activating agent and the nitrogen atom-containing cationic compound, the above-exemplified agents and compounds may be used.

The compounds to be reacted for increasing the cationic properties may be used singly or in combination of two or more of them.

The reaction between the crystalline cellulose or the activated crystalline cellulose and the nitrogen atom-containing cationic compound may be performed, for example, at about 10 to 100° C. for about 0.1 to 24 hours.

The solvent used may typically be water. Alcohols such as methanol, ethanol, 2-propanol, and ethylene glycol monomethyl ether (2-methoxyethanol) and aprotic polar solvents such as dimethylformamide and dimethyl sulfoxide may also be used. The solvents may be used singly or in combination of two or more of them.

The thus-obtained crystalline cellulose having a nitrogen atom-containing cationic group may be a crystalline cellulose to which a nitrogen atom-containing cationic compound is bonded or a crystalline cellulose to which a nitrogen atom-containing cationic compound is bonded through a crosslinking agent.

Properties of Crystalline Cellulose Having Nitrogen Atom-Containing Cationic Group The crystalline cellulose having a nitrogen atom-containing cationic group may comprise the nitrogen atom-containing cationic group at a content of, for example, 0.05 meq/dry·g or more, preferably 0.2 meq/dry·g or more, and more preferably 0.4 meq/dry·g or more, in terms of anion exchange capacity (AEC). Within such a range, ET can be sufficiently adsorbed and removed. The content may be, for example, 10 meq/dry·g or less, preferably 5 meq/dry·g or less, and more preferably 3 meq/dry·g or less. Within such a range, ET can be efficiently removed from a material containing ET to be removed and containing an acidic polymer compound.

The crystalline cellulose having a nitrogen atom-containing cationic group has, as an index content of the nitrogen atom-containing cationic group, an anion exchange capacity (AEC) of, for example, 0.05 to 10 meq/dry·g, 0.05 to 5 meq/dry·g, 0.05 to 3 meq/dry·g, 0.2 to 10 meq/dry·g, 0.2 to 5 meq/dry·g, 0.2 to 3 meq/dry·g, 0.4 to 10 meq/dry·g, 0.4 to 5 meq/dry·g, or 0.4 to 3 meq/dry·g.

The crystalline cellulose having a nitrogen atom-containing cationic group may have a cationic group other than the nitrogen atom-containing cationic group as long as the advantageous effects of the invention are not impaired. The content of the cationic group other than the nitrogen atom-containing cationic group may be, for example, 3 meq/dry·g or less in terms of anion exchange capacity (AEC). The anion-exchange group other than the nitrogen atom-containing cationic group may not be contained. The anion exchange capacity (AEC) as an index content of the cationic group other than the nitrogen atom-containing cationic group is, for example, 0 to 3 meq/dry·g.

If the crystalline cellulose having a nitrogen atom-containing cationic group comprises an anionic group, a cation is nonspecifically adsorbed to the anionic group. Hence, the crystalline cellulose having a nitrogen atom-containing cationic group preferably comprises no anionic group. When an anionic group is contained, the content thereof may be, for example, 1 meq/dry·g or less in terms of cation exchange capacity (CEC). The cation exchange capacity (CEC) as an index content of the anionic group is, for example, 0 to 1 meq/dry·g.

In the present invention, the ion exchange capacity is determined by a pH titration method and is specifically determined in accordance with the method in examples.

The crystalline cellulose to which a nitrogen atom-containing cationic group is introduced may be a particulate cellulose having an average particle size of about 1 to 1,000 μm. The average particle size may be specifically 10 μm or more or 100 μm or more or may be 500 μm or less or 300 μm or less. Within such a range, ET can be efficiently removed from a material containing a substance having a cationic group and is readily separated from an aqueous material containing ET to be removed. The crystalline cellulose to which a nitrogen atom-containing cationic group is introduced has an average particle size of, for example, 1 to 500 μm, 1 to 300 μm, 10 to 1,000 μm, 10 to 500 μm, 10 to 300 μm, 100 to 1,000 μm, 100 to 500 μm, or 100 to 300 μm.

In the present invention, the average particle size is determined by a sieving method.

By introducing a cationic group having a nitrogen atom to a crystalline cellulose, the crystalline cellulose can swell. Hence, the crystalline cellulose after introduction of the cationic group can have a larger average particle size than the average particle size of the original crystalline cellulose.

The crystalline cellulose to which a nitrogen atom-containing cationic group is introduced preferably has a narrow particle size distribution. For example, particles having a D50 of 40 to 60 μm preferably have a D10 of 10 to 30 μm and a D90 of 80 to 120 μm. Within such a range, a stable ET adsorption capacity is exerted.

In the present invention, the particle size distribution is determined by a sieving method.

The crystalline cellulose to which a nitrogen atom-containing cationic group is introduced may have an average polymerization degree of, for example, 50 or more, 100 or more, or 150 or more and may have an average polymerization degree of, for example, 100,000 or less, 10,000 or less, or 5,000 or less. Within such a range, the reaction of introducing a cationic group is readily performed. The crystalline cellulose to which a nitrogen atom-containing cationic group is introduced has an average polymerization degree of, for example, 50 to 100,000, 50 to 10,000, 50 to 5,000, 100 to 100,000, 100 to 10,000, 100 to 5,000, 150 to 100,000, 150 to 10,000, or 150 to 5,000.

In the present invention, the average polymerization degree is determined by viscometry.

The crystalline cellulose to which a nitrogen atom-containing cationic group is introduced may have a bulk density of, for example, 0.01 or more, 0.05 or more, or 0.1 or more and may have a bulk density of, for example, 2 or less, 1 or less, or 0.5 or less. Within such a range, ET can be efficiently removed from a material containing a substance having a cationic group and is readily separated from an aqueous material containing ET to be removed. The crystalline cellulose to which a nitrogen atom-containing cationic group is introduced has a bulk density of, for example, 0.01 to 2, 0.01 to 1, 0.01 to 0.5, 0.05 to 2, 0.05 to 1, 0.05 to 0.5, 0.1 to 2, 0.1 to 1, or 0.1 to 0.5.

In the present invention, the bulk density is determined by using a graduated cylinder.

The crystalline cellulose to which a nitrogen atom-containing cationic group is introduced may have an ET adsorption capacity of, for example, 500 μg or more, 700 μg or more, 800 μg or more, or 850 μg or more, per 1 wet-g. The upper limit of the ET adsorption capacity is not specifically limited and is typically about 1,500 μg. The crystalline cellulose to which a nitrogen atom-containing cationic group is introduced has an ET adsorption capacity of, for example, 500 to 1,500 μg, 700 to 1,500 μg, 800 to 1,500 μg, or 850 to 1,500 μg, per 1 wet-g.

The crystalline cellulose to which a nitrogen atom-containing cationic group is introduced may have an apparent ET dissociation constant of, for example, $2 \times 10^{-11}$ M or less, $1.7 \times 10^{-11}$ M or less, $1.5 \times 10^{-11}$ M or less, or $1.3 \times 10^{-11}$ M or less. The lower limit of the apparent ET dissociation constant is not specifically limited and is typically about $1 \times 10^{-11}$ M. The crystalline cellulose to which a nitrogen atom-containing cationic group is introduced has an apparent ET dissociation constant of, for example, $1 \times 10^{-11}$ to $2 \times 10^{-11}$ M, $1 \times 10^{-11}$ to $1.7 \times 10^{-11}$ M, $1 \times 10^{-11}$ to $1.5 \times 10^{-11}$ M, or $1 \times 10^{-11}$ to $1.3 \times 10^{-11}$ M.

The ET adsorption capacity and the apparent ET dissociation constant are calculated from a linear equation obtained by a Scatchard plot created based on an ET adsorption isotherm and is specifically determined by the following method.

Adsorption is performed in a batch system using 0.1 wet-g of an adsorbent and 4 mL of sample solutions having various ET concentrations. Adsorbed ET concentrations (B) are plotted relative to free ET concentrations (F) to prepare an adsorption isotherm, and based on the adsorption isotherm, the ratios, B/F, are plotted relative to the adsorbed ET concentrations (B) to prepare a Scatchard plot. From the plotted Scatchard plot, a linear equation, y=ax+b, is obtained. When the associated molecular weight of ET is assumed to be $10^6$, the dissociation constant and the adsorption capacity can be expressed by the following equations.

Apparent endotoxin dissociation constant=$1/|a| \times 10^{12}$

Endotoxin adsorption capacity (μg/adsorbent amount (wet-g))=$-(b/a)$

The crystalline cellulose having a nitrogen atom-containing cationic group can be stored, for example, as a dispersion in a dispersion medium such as methanol and ethanol.

ET Adsorbent

The crystalline cellulose having a nitrogen atom-containing cationic group can be used independently or in combination with other components, as the ET adsorbent of the present invention. In other words, the ET adsorbent of the present invention may consist of the crystalline cellulose having a nitrogen atom-containing cationic group or may comprise additional components. The additional component is not specifically limited as long as an intended ET adsorption capacity is achieved.

The ET adsorbent of the present invention in an untreated state is typically a granular substance but may be processed into an intended shape such as a membrane shape and a pillar shape. The shape may be formed, for example, by a papermaking process.

The ET adsorbent of the present invention can be packed in a column and used. The column comprising the ET adsorbent of the present invention therein can be used as a column for removing ET.

The ET adsorbent of the present invention can be treated into an ET-free form as needed and used. The ET-free form can be prepared in a usual manner. Specifically, the ET-free form can be prepared, for example, by washing the ET adsorbent of the present invention once or multiple times with a cleaning liquid. Examples of the cleaning liquid include an aqueous solution of sodium hydroxide and an ethanol solution of sodium hydroxide. After washing, the ET adsorbent of the present invention can be separated from the cleaning liquid by a solid-liquid separating means such as centrifugation and filtration.

(2) ET Removal Method

By bringing the ET adsorbent of the present invention into contact with a material containing ET to be removed, the ET in the material containing ET to be removed is adsorbed to the ET adsorbent. Accordingly, a material from which ET has been removed is obtained. Then, the material from which ET has been removed can be separated from the ET adsorbent that has adsorbed ET.

In other words, the ET removal method of the present invention is a method comprising a step of bringing the ET adsorbent of the present invention into contact with a material containing ET to be removed. The method can further comprise a step of separating a material from which ET has been removed from the ET adsorbent that has adsorbed ET, for example, a step of collecting the material from which ET has been removed from a mixture of the ET adsorbent of the present invention and the material containing ET to be removed. In other words, the ET removal method of the present invention is a method of producing a material from which ET has been removed.

The material containing ET to be removed may be a floating or liquid material. The material containing ET to be removed may be a floating or liquid material made by heating or warming. The material containing ET to be removed may comprise a single component or may comprise two or more components. The material containing ET to be removed may be a solution or suspension of a single or two or more components in water or another solvent. Even when brought into contact with an aqueous composition, the ET adsorbent of the present invention is easily separated from the aqueous composition after contact. Hence, the material containing ET to be removed is preferably a material containing water.

Examples of the material containing ET to be removed include water for medical use such as distilled water for injection and saline for injection, injection fluids, and water for food preparation.

As described above, the ET adsorbent of the present invention can be suitably used for removal of ET from a material containing a substance having a cationic group or a highly viscous material. Examples of the material containing ET to be removed include mucopolysaccharides such as chondroitin sulfate, hyaluronic acid, sodium hyaluronate, heparan sulfate, dermatan sulfate, keratan sulfate, and heparin. Mucopolysaccharides are used as a component in pharmaceutical products, cosmetics, and the like.

Examples of the material containing a substance having a cationic group include polysaccharides containing an amino sugar such as glucosamine as a building block, including chitin and chitosan; and basic amino acid-containing polypeptides including gelatin, collagen, and polylysine. These materials are used as a component in pharmaceutical products, dietary supplements, cosmetics, and the like or as a thickener, a gelling agent, or an adhesive paste.

Examples of the highly viscous material containing ET to be removed include β-glucans such as laminaran, curdlan, and cellulose; α-glucans such as pullulan, amylose, glycogen, amylopectin, and dextran; and an aqueous solution of decomposed collagen. These materials are used as a component in pharmaceutical products, dietary supplements, cosmetics, and the like or as a food additive.

Examples of the highly viscous material containing ET to be removed also include polysaccharides such as alginic acid, sodium alginate, pectin, carrageenan, guar gum, locust bean gum, tamarind gum, and xanthan gum, propylene glycol, and carboxymethyl cellulose. These materials are used as a thickener, a gelling agent, an adhesive paste, or the like for production of pharmaceutical or food products.

A material prepared by decomposition of such a material with an acid, an alkali, or an enzyme may also be used.

Examples of the highly viscous material containing ET to be removed also include monomers used as a material of artificial organs or artificial bones.

A solution or suspension prepared by dissolving or suspending such a material in water or another solvent can also be used as the material containing ET to be removed.

Other examples of the material containing ET to be removed include solutions or suspensions of proteins, peptides, vitamins, and the like.

When brought into contact with the ET adsorbent of the present invention, the material containing ET to be removed can have various pH values depending on the type of a cationic group, the pH stability of the material containing ET to be removed, and the like. For example, the pH can be about 1 to 14, particularly about 3 or more, about 4 or more, about 5 or more, or about 6 or more and can be about 10 or less, about 9 or less, or about 8 or less. The pH may be about 7 or less. When brought into contact with the ET adsorbent of the present invention, the material containing ET to be removed has a pH of, for example, 1 to 10, 1 to 9, 1 to 8, 1 to 7, 3 to 14, 3 to 10, 3 to 9, 3 to 8, 3 to 7, 4 to 14, 4 to 10, 4 to 9, 4 to 8, 4 to 7, 5 to 14, 5 to 10, 5 to 9, 5 to 8, 5 to 7, 6 to 14, 6 to 10, 6 to 9, 6 to 8, or 6 to 7.

When brought into contact with the ET adsorbent of the present invention, the material containing ET to be removed can have various ionic strengths depending on the type of a cationic group, the ionic strength stability of the material containing ET to be removed, and the like. For example, the ionic strength can be about 0.8 or less, about 0.6 or less, or about 0.4 or less. The ionic strength can be zero or practically zero or can be about 0.001 or more, about 0.003 or more, or about 0.005 or more. When brought into contact with the ET adsorbent of the present invention, the material containing ET to be removed has an ionic strength of, for example, 0 to 0.8, 0 to 0.6, 0 to 0.4, 0.001 to 0.8, 0.001 to 0.6, 0.001 to 0.4, 0.003 to 0.8, 0.003 to 0.6, 0.003 to 0.4, 0.005 to 0.8, 0.005 to 0.6, or 0.005 to 0.4.

The ET adsorbent of the present invention can be brought into contact with the material containing ET to be removed, for example, in a batch system. The "batch system" is a system by mixing the ET adsorbent of the present invention with a material containing ET to be removed in an appropriate container, thereby bringing the ET adsorbent of the present invention into contact with the material containing ET to be removed. In the batch system, a mixture may be allowed to stand or may be stirred or shaken. The contact time varies with the type of a material containing ET to be removed and the like and can be, for example, about 5 minutes to 120 hours, about 30 minutes to 24 hours, about 1 to 12 hours, or about 2 to 4 hours. The temperature at the time of contact varies with the type of a material containing ET to be removed and the like and can be, for example, about 5 to 80° C., about 15 to 65° C., or about 25 to 50° C. After adsorption of ET to the ET adsorbent of the present invention, the ET adsorbent of the present invention can be separated from the mixture by filtration, centrifugation, or the like.

The ET adsorbent of the present invention can be brought into contact with a material containing ET to be removed, for example, by a fluidizing separation method. The "fluidizing separation method" is a technique by allowing a material containing ET to be removed to pass through the ET adsorbent of the present invention, thereby bringing the ET adsorbent of the present invention into contact with the material containing ET to be removed. Specifically, for example, by packing the ET adsorbent of the present invention in a column and allowing an ET-containing liquid to pass through the column, the ET adsorbent of the present invention can be brought into contact with the material containing ET to be removed. For example, when the ET adsorbent of the present invention is formed into a filter shape, by allowing a material containing ET to be removed to pass through the filter, the ET adsorbent of the present invention can be brought into contact with the material containing ET to be removed. Examples of the membrane include a membrane filter, a hollow fiber membrane, and a tubular membrane. When the ET adsorbent of the present invention is formed into a pillar shape or the like, by allowing a material containing ET to be removed to pass through the pillar-shaped adsorbent or the like, the ET adsorbent of the present invention can be brought into contact with the material containing ET to be removed. The pillar-shaped adsorbent, which is, for example, a continuous porous body having micropores can be served for monolith chromatography. By placing the ET adsorbent of the present invention on a filter paper and allowing a material containing ET to be removed to pass therethrough, the ET adsorbent of the present invention can be brought into contact with the material containing ET to be removed.

By the ET removal method of the present invention, ET in a material containing ET to be removed is removed. The ET can be removed to such a degree that the ET concentration or content in a material containing ET to be removed after the treatment (after contact with the ET adsorbent of the present invention) is lower than that before the treatment (before contact with the ET adsorbent of the present invention).

The "ET being removed" may mean that, for example, the ET concentration or content in the material containing ET to be removed after treatment is reduced, as compared with that before the treatment, to 50% or less, 30% or less, 20% or less, 10% or less, 5% or less, 2% or less, or 1% or less. As an index of the "ET being removed", the proportion of the ET concentration or content in the material containing ET to be removed after the treatment relative to that before the treatment is, for example, 0 to 50%, 0 to 30%, 0 to 20%, 0 to 10%, 0 to 5%, 0 to 2%, or 0 to 1%.

The "ET being removed" may mean that, for example, the liquid after the treatment has an ET concentration of 10 EU/mL or less, 7 EU/mL or less, 5 EU/mL or less, 1 EU/mL or less, 0.5 EU/mL or less, 0.2 EU/mL or less, 0.1 EU/mL or less, 0.05 EU/mL or less, 0.02 EU/mL or less, 0.01 EU/mL or less, 0.005 EU/mL or less, 0.002 EU/mL or less, or 0.001 EU/mL or less. As an index of the "ET being removed", the concentration of ET in the liquid after the treatment is, for example, 0 to 10 EU/mL, 0 to 7 EU/mL, 0 to 5 EU/mL, 0 to 1 EU/mL, 0 to 0.5 EU/mL, 0 to 0.2 EU/mL, 0 to 0.1 EU/mL, 0 to 0.05 EU/mL, 0 to 0.02 EU/mL, 0 to 0.01 EU/mL, 0 to 0.005 EU/mL, 0 to 0.002 EU/mL, or 0 to 0.001 EU/mL.

The ET removal method of the present invention may remove ET also from a material containing ET to be removed and having a low ET concentration or content. For example, the method may remove ET from a material containing ET to be removed and having an ET concentration of 40 EU/mL or less, 30 EU/mL or less, 20 EU/mL or less, or 10 EU/mL or less (for example, 0 to 40 EU/mL, 0 to 30 EU/mL, 0 to 20 EU/mL, or 0 to 10 EU/mL) so as to give an ET concentration of 7 EU/mL or less, 5 EU/mL or less, 1 EU/mL or less, 0.5 EU/mL or less, 0.2 EU/mL or less, 0.1 EU/mL or less, 0.05 EU/mL or less, 0.02 EU/mL or less, 0.01 EU/mL or less, 0.005 EU/mL or less, 0.002 EU/mL or less, or 0.001 EU/mL or less (for example, 0 to 7 EU/mL, 0 to 5 EU/mL, 0 to 1 EU/mL, 0 to 0.5 EU/mL, 0 to 0.2 EU/mL, 0 to 0.1 EU/mL, 0 to 0.05 EU/mL, 0 to 0.02 EU/mL, 0 to 0.01 EU/mL, 0 to 0.005 EU/mL, 0 to 0.002 EU/mL, or 0 to 0.001 EU/mL).

The present invention encompasses materials including a mucopolysaccharide, a basic amino acid-containing polypeptide, a polysaccharide, propylene glycol, and carboxymethyl cellulose, having an ET content of 600 EU/g or less, 500 EU/g or less, 100 EU/g or less, 50 EU/g or less, 20 EU/g or less, 10 EU/g or less, 7 EU/g or less, 5 EU/g or less, 1 EU/g or less, 0.5 EU/g or less, or 0.2 EU/g or less (for example, 0 to 600 EU/g, 0 to 500 EU/g, 0 to 100 EU/g, 0 to 50 EU/g, 0 to 20 EU/g, 0 to 10 EU/g, 0 to 7 EU/g, 0 to 5 EU/g, 0 to 1 EU/g, 0 to 0.5 EU/g, or 0 to 0.2 EU/g), and encompasses a solution (particularly an aqueous solution) of such a material. Examples of the mucopolysaccharide, the basic amino acid-containing polypeptide, and the polysaccharide include those exemplified as the material containing ET to be removed.

"EU/g" represents the ET amount (EU) per solid content weight (g) of the material after ET removal.

The present invention also encompasses materials including a mucopolysaccharide, a basic amino acid-containing polypeptide, a polysaccharide, propylene glycol, and carboxymethyl cellulose, having an ET concentration of 6 EU/mL or less, 5 EU/mL or less, 1 EU/mL or less, 0.5 EU/mL or less, 0.1 EU/mL or less, 0.05 EU/mL or less, 0.01 EU/mL or less, 0.005 EU/mL or less, or 0.002 EU/mL or less (for example, 0 to 6 EU/mL, 0 to 5 EU/mL, 0 to 1 EU/mL, 0 to 0.5 EU/mL, 0 to 0.1 EU/mL, 0 to 0.05 EU/mL, 0 to 0.01 EU/mL, 0 to 0.005 EU/mL, or 0 to 0.002 EU/mL), and encompasses a solution (particularly an aqueous solution) of such a material.

Specifically, a natural glucan (particularly α-glucan, specifically pullulan) has a high ET content, but according to the present invention, a glucan (particularly α-glucan, specifically pullulan) having an ET content of 600 EU/g or less, 500 EU/g or less, 100 EU/g or less, 50 EU/g or less, 20 EU/g or less, 10 EU/g or less, 7 EU/g or less, 5 EU/g or less, 1 EU/g or less, 0.5 EU/g or less, or 0.2 EU/g or less (for example, 0 to 500 EU/g, 0 to 100 EU/g, 0 to 50 EU/g, 0 to 20 EU/g, 0 to 10 EU/g, 0 to 7 EU/g, 0 to 5 EU/g, 0 to 1 EU/g, 0 to 0.5 EU/g, or 0 to 0.2 EU/g) in 1 g of the solid content of the glucan (particularly α-glucan, specifically pullulan) or a solution (particularly an aqueous solution) thereof can be provided.

According to the present invention, a glucan (particularly α-glucan, specifically pullulan) having an ET concentration of 6 EU/mL or less, 5 EU/mL or less, 1 EU/mL or less, 0.5 EU/mL or less, 0.1 EU/mL or less, 0.05 EU/mL or less, 0.01 EU/mL or less, 0.005 EU/mL or less, or 0.002 EU/mL or less (for example, 0 to 6 EU/mL, 0 to 5 EU/mL, 0 to 1 EU/mL, 0 to 0.5 EU/mL, 0 to 0.1 EU/mL, 0 to 0.05 EU/mL, 0 to 0.01 EU/mL, 0 to 0.005 EU/mL, or 0 to 0.002 EU/mL) or a solution (particularly an aqueous solution) thereof can also be provided.

In the solution (particularly the aqueous solution), the glucan (particularly α-glucan, specifically pullulan) concentration can be 1% by weight or more, 5% by weight or more, or 8% by weight or more and be 20% by weight or less, 15% by weight or less, or 12% by weight or less (for example, 1 to 20% by weight, 1 to 15% by weight, 1 to 12% by weight, 5 to 20% by weight, 5 to 15% by weight, 5 to 12% by weight, 8 to 20% by weight, 8 to 15% by weight, or 8 to 12% by weight).

When the glucan (particularly α-glucan, specifically pullulan) concentration is 10% by weight, a glucan (particularly α-glucan, specifically pullulan) having an ET content of 600 EU/g or less, 500 EU/g or less, 100 EU/g or less, 50 EU/g or less, 20 EU/g or less, 10 EU/g or less, 7 EU/g or less, 5 EU/g or less, 1 EU/g or less, 0.5 EU/g or less, or 0.2 EU/g or less (for example, 0 to 600 EU/g, 0 to 500 EU/g, 0 to 100 EU/g, 0 to 50 EU/g, 0 to 20 EU/g, 0 to 10 EU/g, 0 to 7 EU/g, 0 to 5 EU/g, 0 to 1 EU/g, 0 to 0.5 EU/g, or 0 to 0.2 EU/g) in 1 g of the solid content of the glucan (particularly α-glucan, specifically pullulan) or a solution (particularly an aqueous solution) thereof is also provided.

When the glucan (particularly α-glucan, specifically pullulan) concentration is 10% by weight, a glucan (particularly α-glucan, specifically pullulan) having an ET concentration of 6 EU/mL or less, 5 EU/mL or less, 1 EU/mL or less, 0.5 EU/mL or less, 0.1 EU/mL or less, 0.05 EU/mL or less, 0.01 EU/mL or less, 0.005 EU/mL or less, or 0.002 EU/mL or less (for example, 0 to 6 EU/mL, 0 to 5 EU/mL, 0 to 1 EU/mL, 0 to 0.5 EU/mL, 0 to 0.1 EU/mL, 0 to 0.05 EU/mL, 0 to 0.01 EU/mL, 0 to 0.005 EU/mL, or 0 to 0.002 EU/mL) or a solution (particularly an aqueous solution) thereof is also provided.

According to the present invention, a gelatin or gelatin degradation product having an ET content of 600 EU/g or less, 500 EU/g or less, 100 EU/g or less, 50 EU/g or less, 20 EU/g or less, 10 EU/g or less, 7 EU/g or less, 5 EU/g or less, 1 EU/g or less, 0.5 EU/g or less, or 0.2 EU/g or less (for example, 0 to 600 EU/g, 0 to 500 EU/g, 0 to 100 EU/g, 0 to 50 EU/g, 0 to 20 EU/g, 0 to 10 EU/g, 0 to 7 EU/g, 0 to 5 EU/g, 0 to 1 EU/g, 0 to 0.5 EU/g, or 0 to 0.2 EU/g) in 1 g of the solid content of the gelatin or gelatin degradation product or a solution (particularly an aqueous solution) thereof is provided.

According to the present invention, a gelatin or gelatin degradation product having an ET concentration of 6 EU/mL or less, 5 EU/mL or less, 1 EU/mL or less, 0.5 EU/mL or less, 0.1 EU/mL or less, 0.05 EU/mL or less, 0.01 EU/mL or less, 0.005 EU/mL or less, or 0.002 EU/mL or less (for example, 0 to 6 EU/mL, 0 to 5 EU/mL, 0 to 1 EU/mL, 0 to 0.5 EU/mL, 0 to 0.1 EU/mL, 0 to 0.05 EU/mL, 0 to 0.01 EU/mL, 0 to 0.005 EU/mL, or 0 to 0.002 EU/mL) or a solution (particularly an aqueous solution) thereof is also provided.

In the solution (particularly the aqueous solution), the concentration of the gelatin or gelatin degradation product can be 0.1% by weight or more, 0.5% by weight or more, or 0.8% by weight or more and be 2% by weight or less, 1.5% by weight or less, or 1.2% by weight or less (for example, 0.1 to 2% by weight, 0.1 to 1.5% by weight, 0.1 to 1.2% by weight, 0.5 to 2% by weight, 0.5 to 1.5% by weight, 0.5 to 1.2% by weight, 0.8 to 2% by weight, 0.8 to 1.5% by weight, or 0.8 to 1.2% by weight).

When the gelatin or gelatin degradation product concentration is 1% by weight, a gelatin or gelatin degradation product having an ET content of 600 EU/g or less, 500 EU/g or less, 100 EU/g or less, 50 EU/g or less, 20 EU/g or less, 10 EU/g or less, 7 EU/g or less, 5 EU/g or less, 1 EU/g or less, 0.5 EU/g or less, or 0.2 EU/g or less (for example, 0 to 600 EU/g, 0 to 500 EU/g, 0 to 100 EU/g, 0 to 50 EU/g, 0 to 20 EU/g, 0 to 10 EU/g, 0 to 7 EU/g, 0 to 5 EU/g, 0 to 1 EU/g, 0 to 0.5 EU/g, or 0 to 0.2 EU/g) in 1 g of the solid content of the gelatin or gelatin degradation product or a solution (particularly an aqueous solution) thereof is also provided.

When the gelatin or gelatin degradation product concentration is 1% by weight, a gelatin or gelatin degradation product having an ET concentration of 6 EU/mL or less, 5 EU/mL or less, 1 EU/mL or less, 0.5 EU/mL or less, 0.1 EU/mL or less, 0.05 EU/mL or less, 0.01 EU/mL or less, 0.005 EU/mL or less, or 0.002 EU/mL or less (for example, 0 to 6 EU/mL, 0 to 5 EU/mL, 0 to 1 EU/mL, 0 to 0.5 EU/mL, 0 to 0.1 EU/mL, 0 to 0.05 EU/mL, 0 to 0.01 EU/mL, 0 to 0.005 EU/mL, or 0 to 0.002 EU/mL) or a solution (particularly an aqueous solution) thereof is also provided.

In particular, according to the present invention, a collagen having an ET content of 600 EU/g or less, 500 EU/g or less, 100 EU/g or less, 50 EU/g or less, 20 EU/g or less, 10 EU/g or less, 7 EU/g or less, 5 EU/g or less, 1 EU/g or less, 0.5 EU/g or less, or 0.2 EU/g or less (for example, 0 to 600 EU/g, 0 to 500 EU/g, 0 to 100 EU/g, 0 to 50 EU/g, 0 to 20 EU/g, 0 to 10 EU/g, 0 to 7 EU/g, 0 to 5 EU/g, 0 to 1 EU/g, 0 to 0.5 EU/g, or 0 to 0.2 EU/g) in 1 g of the solid content of the collagen or a solution (particularly an aqueous solution) thereof is provided.

According to the present invention, a collagen having an ET concentration of 6 EU/mL or less, 5 EU/mL or less, 1 EU/mL or less, 0.5 EU/mL or less, 0.1 EU/mL or less, 0.05 EU/mL or less, 0.01 EU/mL or less, 0.005 EU/mL or less, or 0.002 EU/mL or less (for example, 0 to 6 EU/mL, 0 to 5 EU/mL, 0 to 1 EU/mL, 0 to 0.5 EU/mL, 0 to 0.1 EU/mL, 0 to 0.05 EU/mL, 0 to 0.01 EU/mL, 0 to 0.005 EU/mL, or 0 to 0.002 EU/mL) or a solution (particularly an aqueous solution) thereof is also provided.

In the solution (particularly the aqueous solution), the collagen concentration can be 0.01% by weight or more, 0.05% by weight or more, or 0.08% by weight or more and be 0.2% by weight or less, 0.15% by weight or less, or 0.12% by weight or less (for example, 0.01 to 0.2% by weight, 0.01 to 0.15% by weight, 0.01 to 0.12% by weight, 0.05 to 0.2% by weight, 0.05 to 0.15% by weight, 0.05 to 0.12% by weight, 0.08 to 0.2% by weight, 0.08 to 0.15% by weight, or 0.08 to 0.12% by weight).

When the collagen concentration is 0.1% by weight, a collagen having an ET content of 500 EU/g or less, 100 EU/g or less, 50 EU/g or less, 20 EU/g or less, 10 EU/g or less, 7 EU/g or less, 5 EU/g or less, 1 EU/g or less, 0.5 EU/g or less, or 0.2 EU/g or less (for example, 0 to 500 EU/g, 0 to 100 EU/g, 0 to 50 EU/g, 0 to 20 EU/g, 0 to 10 EU/g, 0 to 7 EU/g, 0 to 5 EU/g, 0 to 1 EU/g, 0 to 0.5 EU/g, or 0 to 0.2 EU/g) in 1 g of the solid content of the collagen or a solution (particularly an aqueous solution) thereof is also provided.

When the collagen concentration is 0.1% by weight, a collagen having an ET concentration of 6 EU/mL or less, 5 EU/mL or less, 1 EU/mL or less, 0.5 EU/mL or less, 0.1 EU/mL or less, 0.05 EU/mL or less, 0.01 EU/mL or less, 0.005 EU/mL or less, or 0.002 EU/mL or less (for example, 0 to 6 EU/mL, 0 to 5 EU/mL, 0 to 1 EU/mL, 0 to 0.5 EU/mL, 0 to 0.1 EU/mL, 0 to 0.05 EU/mL, 0 to 0.01 EU/mL, 0 to 0.005 EU/mL, or 0 to 0.002 EU/mL) or a solution (particularly an aqueous solution) thereof is also provided.

When the material containing ET to be removed is a solution or suspension of a particular component that is to be separated from ET, the particular component is not removed after treatment. "A particular component in a material containing ET to be removed being not removed" may mean that the content of the particular component in the material containing ET to be removed after treatment is maintained at 90% or more, 95% or more, 97% or more, or 99% or more as compared with that before treatment. The proportion of the content of a particular component in the material containing ET to be removed after treatment relative to that before treatment is, for example, 90 to 100%, 95 to 100%, 97 to 100%, or 99 to 100%.

Removal of ET is ascertained by quantitative determination of the ET in the material containing ET to be removed after treatment. Examples of the quantitative determination method of ET include a Limulus test using a Limulus reagent. The Limulus test can be performed in a usual manner. The Limulus test can be performed, for example, by a colorimetric method, a turbidimetric method, or a gelation method.

EXAMPLES

The present invention will next be described in more detail with reference to Examples, but the present invention is not limited to them.

(1) Production of Cationized Microcrystalline Cellulose

As cationized crystalline celluloses, ethylenediamine- (EDA-) immobilized crystalline cellulose, hexamethylenediamine- (HMDA-) immobilized crystalline cellulose, tetraethylenepentamine- (TEPA-) immobilized crystalline cellulose, N,N,N',N'-tetramethyl-1,6-diaminohexane- (TMDH-) immobilized crystalline cellulose, tetramethylethylenediamine- (TMEDA-) immobilized crystalline cellulose, arginine- (Arg-) immobilized crystalline cellulose, polyethyleneimine- (PEI-) immobilized crystalline cellulose, quaternized tetraethylenepentamine- (Q-TEPA-) immobilized crystalline cellulose, glycidyltrimethylammonium- (GTMA-) immobilized crystalline cellulose, and epoxy polymer-modified TMDH-immobilized microcrystalline cellulose (Ep-TMDH-MCC) were synthesized by the following procedures.

Example 1

In a 500-ml four-necked flask, 15 g of microcrystalline cellulose (comprecel 101; FUSHIMI Pharmaceutical Co., Ltd.) and a 20% (w/w) aqueous potassium hydroxide solution (42.4 g of potassium hydroxide (extra pure reagent; Wako Pure Chemical Industries, Ltd.) dissolved in 169.6 ml of water) were placed, and the whole was stirred in a water bath at 30° C. for 1 hour. Next, into the four-necked flask, 113 ml of chloromethyloxirane (guaranteed reagent; Wako Pure Chemical Industries, Ltd.) was added, and the whole was stirred in a water bath at 40° C. for 2 hours. The reaction product was subjected to suction filtration through a filter cloth (TF-301B; an air permeability of 10.2 cc/cm$^2$/sec; Toray Industries Inc.) to give an epoxy activated microcrystalline cellulose (Ep-MCC) as a solid content (filtration residue).

The obtained Ep-MCC was placed in a 500-ml four-necked flask and was dispersed in 141.3 ml of water. Then, a 50% (w/w) aqueous EDA solution (a mixed solution of 20.8 ml of EDA (guaranteed reagent; Wako Pure Chemical Industries, Ltd.) and 20.8 ml of water) was added dropwise, and the whole was stirred in a water bath at 50° C. for 2 hours. The reaction product was subjected to suction filtration through a filter cloth and was washed with ultrapure water. The obtained solid content (filtration residue) was placed in a 500-ml four-necked flask and was stirred in 200 ml of water at room temperature for 1 hour. The mixture was subjected to suction filtration through a filter cloth and washed with ultrapure water and methanol, giving EDA-immobilized microcrystalline cellulose (hereinafter also called "EDA-MCC").

Example 2

Ep-MCC was prepared in the same manner as in Example 1, then the Ep-MCC and 98 ml of water were placed in a 500-ml four-necked flask, and the whole was stirred. Then, a 50% (w/w) aqueous HMDA solution (a mixed solution of 42.5 ml of HMDA (extra pure reagent; Wako Pure Chemical Industries, Ltd.) and 42.5 ml of water) was added dropwise, and the whole was stirred in a water bath at 50° C. for 2 hours. Then, the same procedure as in Example 1 was performed, giving HMDA immobilized microcrystalline cellulose (hereinafter also called "HMDA-MCC").

Example 3

Ep-MCC was prepared in the same manner as in Example 1, then the Ep-MCC and 62.8 ml of water were placed in a 500-ml four-necked flask, and the whole was stirred. Next, a 50% (w/w) aqueous TEPA solution (a mixed solution of 59.3 ml of TEPA (Tokyo Chemical Industry Co., Ltd.) and 59.3 ml of water) was added dropwise, and the whole was stirred in a water bath at 50° C. for 2 hours. Then, the same procedure as in Example 1 was performed, giving TEPA-immobilized microcrystalline cellulose (hereinafter also called "TEPA-MCC").

Example 4

Ep-MCC was prepared in the same manner as in Example 1, then the Ep-MCC and 46.9 ml of water were placed in a 500-ml four-necked flask, and the whole was stirred. Next, a 50% (w/w) aqueous TMDH solution (a mixed solution of 68 ml of TMDH (Tokyo Chemical Industry Co., Ltd.) and 68 ml of water) was added dropwise, and the whole was stirred in a water bath at 50° C. for 19 hours. Then, the same procedure as in Example 1 was performed, giving TMDH-immobilized microcrystalline cellulose (hereinafter also called "TMDH-MCC").

Example 5

Ep-MCC was prepared in the same manner as in Example 1, then the Ep-MCC and 53 ml of water were placed in a 500-ml four-necked flask, and the whole was stirred. Next, a 50% (w/w) aqueous TMEDA solution (a mixed solution of 51 ml of TMEDA (Tokyo Chemical Industry Co., Ltd.) and 51 ml of water) was added dropwise, and the whole was stirred in a water bath at 50° C. for 19 hours. Then, the same procedure as in Example 1 was performed, giving TMEDA-immobilized microcrystalline cellulose (hereinafter also called "TMEDA-MCC").

Example 6

Ep-MCC was prepared in the same manner as in Example 1, then the Ep-MCC, 53.3 g of L(+)-arginine (guaranteed reagent; Wako Pure Chemical Industries, Ltd.), and 162 ml of water were placed in a 500-ml four-necked flask, and the whole was stirred in a water bath at 50° C. for 2 hours. Then, the same procedure as in Example 1 was performed, giving Arg-immobilized microcrystalline cellulose (hereinafter also called "Arg-MCC").

Example 7

Ep-MCC was prepared in the same manner as in Example 1, then the Ep-MCC and 132.4 ml of water were placed in a 500-ml four-necked flask, and the whole was stirred. Next, a 50% (w/w) aqueous polyethyleneimine solution (a mixed solution of 25.4 ml of polyethyleneimine (an average molecular weight of 1,800; Wako Pure Chemical Industries, Ltd.) and 25.4 ml of water) was added dropwise, and the whole was stirred in a water bath at 50° C. for 2 hours. Then, the same procedure as in Example 1 was performed, giving PEI-immobilized microcrystalline cellulose (hereinafter also called "PEI-MCC").

Example 8

In a 50-ml screw tube, 3 g of the TEPA-MCC synthesized in Example 3, 15 ml of water, and 3 ml of chloromethyloxirane were placed, and the whole was stirred in a water bath at 50° C. for 5 hours. The reaction product was subjected to suction filtration through a filter cloth and washed with ultrapure water and methanol, giving Q-TEPA-immobilized microcrystalline cellulose (Q-TEPA-MCC).

Example 9

In a 300-ml four-necked flask, 15 g of microcrystalline cellulose and a 37.5% (w/w) aqueous potassium hydroxide solution (66 g of potassium hydroxide dissolved in 110 ml of water) were placed, and the whole was stirred in a water bath at 30° C. for 1 hour. Next, 32.6 g of a 80% aqueous glycidyltrimethylammonium chloride solution (Tokyo Chemical Industry Co., Ltd.) was added into the four-necked flask, and the whole was stirred in a water bath at 40° C. for 2 hours. The reaction product was subjected to suction filtration through a filter cloth and was washed with ultrapure water and methanol, giving GTMA-immobilized microcrystalline cellulose (hereinafter also called "GTMA-MCC").

Example 10

In a 100-ml four-necked flask, 5 g of the TMDH-MCC synthesized in Example 4, 45 ml of water, and 4.1 ml of ethylene glycol glycidyl ether were placed, and the whole was stirred in a water bath at 50° C. for 1 hour. Next, 6.0 ml of TMDH was added dropwise, and the whole was further stirred for 2 hours. The reaction product was subjected to suction filtration through a filter cloth and was washed with ultrapure water and methanol, giving epoxy polymer-modified TMDH-MCC (Ep-TMDH-MCC).

(2) Measurement of Anion Exchange Capacity

The anion exchange capacity (AEC) of the synthesized, cationized microcrystalline cellulose was determined as an index of the introduction amount of an amino group or another cation group. The AEC was determined by a back-titration method using hydrochloric acid. The procedure will be described below.

Each cationized crystalline cellulose was dried under reduced pressure for 24 hours or more at room temperature, and about 0.5 g of the dried product was accurately weighed in a screw tube. Into the tube, 20 ml of a 0.1 mol/l hydrochloric acid with a known factor was added, and the whole was stirred on a roller for 2 hours. The mixture was filtered through a filter paper, and the filtrate was collected in another 10-ml screw tube. Titration was performed by using a 0.05 mol/l aqueous sodium hydroxide solution with a known factor using phenolphthalein as an indicator.

AEC was calculated in accordance with the following equation.

$$AEC(mEq/dry \cdot g) = (0.1 \times f_{HCl} \times 20 - 0.05 \times f_{NaOH} \times V \times 20/10)/W$$

$f_{HCl}$ factor of used hydrochloric acid
$f_{NaOH}$ factor of used sodium hydroxide
V: titer (ml)
W: particle dry weight (dry·g)

As a result, EDA-MCC had an AEC of 0.7011, HMDA-MCC had an AEC of 0.6480, TEPA-MCC had an AEC of 1.345, TMDH-MCC had an AEC of 0.5563, TMEDA-MCC had an AEC of 0.6661, Arg-MCC had an AEC of 0.4909, PEI-MCC had an AEC of 1.902, Q-TEPA-MCC had an AEC of 0.4583, GTMA-MCC had an AEC of 0.6151, and Ep-TMDH-MCC had an AEC of 0.3836.

(3) ET Adsorption Capacity Evaluation

Each ET adsorption capacity of EDA-MCC, TMDH-MCC, and Arg-MCC prepared in Examples 1, 4, and 6 was determined and compared with the ET adsorption capacity of polylysine-carrying spherical cellulose (Poly(ε-lysine)-cellulose beads; J. LIQ. CHROM. & REL. TECHNOL., 2002, 25 (4): 601-614.) as a known ET adsorbent. The polylysine-carrying spherical cellulose used was ET-clean (trade name) manufactured by JNC.

EDA-MCC, TMDH-MCC, and Arg-MCC prepared in Examples 1, 4, and 6 had AECs of 0.7011, 0.5563, and 0.4909, respectively, as described above. The AEC of the polylysine-carrying spherical cellulose was determined in accordance with the method described in "(2) Measurement of anion exchange capacity" to be 0.9394 meq/g.

The ET adsorption capacity was evaluated in a batch system.

Dry heat sterilizable instruments (conical beakers, transfer pipettes, pipettes, glass filters, spoons, Limulus tubes, and tube caps) were thoroughly washed and then was sterilized at 250° C. for 4 hours. Syringes, membrane filters, and chips used were previously sterilized by α-ray irradiation. The pure water used was Otsuka Distilled Water (Otsuka Pharmaceutical Factory, Inc.).

The ET concentration was determined by using a commercially available Limulus reagent, Endospecy ES-24M (SEIKAGAKU CORPORATION).

Each adsorbent (polylysine-carrying spherical cellulose, EDA-MCC, TMDH-MCC, Arg-MCC) was washed 5 times on a glass filter with 25 ml of 0.2 M NaOH/95% EtOH. Next, washing was repeated with sterilized pure water until the filtrate became neutral.

In a 50-ml conical beaker, the washed adsorbent was weighed, then 10 ml of a material containing ET to be removed shown in Table 1 was added, and the whole was shaken at 200 rpm for 2 hours in a bioshaker at a temperature shown in Table 1. As the material containing ET to be removed, a 10 wt % aqueous pullulan solution, a 1 wt % aqueous solution of alkaline treated gelatin, a 1 wt % aqueous solution of acid treated gelatin, and a 0.1 wt % porcine collagen/5 mM acetic acid solution were used. The pH and the ionic strength of each material containing ET to be removed are as shown in Table 1. The pH and the ionic strength are almost the same as those after mixing of each material containing ET to be removed with the respective adsorbents.

Next, an aqueous solution containing an adsorbent was sucked by a syringe and was filtered through a 0.8-μm membrane filter. The filtrate was diluted with Otsuka Water 10 to 1,000 times. In each test tube containing the Limulus reagent, 0.2 ml of the diluted liquid was placed, and the whole was thoroughly mixed with a vortex mixer. The test tube was installed in an EG Reader SV-12 (SEIKAGAKU CORPORATION), and the residual ET concentration was determined by a kinetic colorimetric method.

The concentration of ET contained in each material containing ET to be removed before contact with the adsorbent was determined in a similar manner to the above: each material containing ET to be removed was filtered through a 0.8-μm membrane filter; then the filtrate was diluted with Otsuka Water 10 to 1,000 times; and the concentration was determined using the Limulus reagent by the kinetic colorimetric method.

The results are shown in Table 1.

TABLE 1

| | | Adsorbent conditions | | | Poly(ε-lysine)-cellulose beads | | | EDA-MCC (Example 1) | |
| --- | --- | --- | --- | --- | --- | --- | --- | --- | --- |
| | | | | | LPS concentration before | LPS concentration after | | LPS concentration before | LPS concentration after |
| Material containing ET to be removed | Adsorbent amout (wet-g) | Temperature (° C.) | pH | Ionic strength | treatment Upper: EU/ml Lower: EU/g | treatment Upper: EU/ml Lower: EU/g | Adsorption rate (%) | treatment Upper: EU/ml Lower: EU/g | treatment Upper: EU/ml Lower: EU/g |
| 10 wt % aqueous pullulan solution | 0.5 | 25 | 7.1 | 0 | 76.4 764 | 5.25 52.5 | 93.1 | 173.0 1730 | 0.66 6.6 |
| 1 wt % aqueous solution of alkaline treated gelatin | 1 | 60 | 6.3 | 0 | 12.97 1297 | 5.63 563 | 56.6 | 12.97 1297 | 4.90 490 |

TABLE 1-continued

| Material | | | | | LPS before | LPS after | Adsorption rate | | |
|---|---|---|---|---|---|---|---|---|---|
| 1 wt % aqueous solution of acid treated gelatin | 1 | 50 | 4.9 | 0 | 10.14 / 1014 | 5.51 / 551 | 45.7 | — | — |
| 0.1 wt % porcine collagen/5 mM acetic acid solution | 0.5 | 25 | 3.7 | 0.005 | 0.024 / 24 | 0.0035 / 3.5 | 85.4 | — | — |

| | | TMDH-MCC (Example 4) | | | Arg-MCC (Example 6) | | |
|---|---|---|---|---|---|---|---|
| Material containing ET to be removed | EDA-MCC (Example 1) Adsorption rate (%) | LPS concentration before treatment Upper: EU/ml Lower: EU/g | LPS concentration after treatment Upper: EU/ml Lower: EU/g | Adsorption rate (%) | LPS concentration before treatment Upper: EU/ml Lower: EU/g | LPS concentration after treatment Upper: EU/ml Lower: EU/gg | Adsorption rate (%) |
| 10 wt % aqueous pullulan solution | 99.6 | 76.4 / 764 | <0.02 / <0.2 | >99.9 | 173.8 / 1730 | 0.02 / 0.2 | 99.9 |
| 1 wt % aqueous solution of alkaline treated gelatin | 62.2 | 13.18 / 1318 | <0.01 / <1 | >99.9 | 16.25 / 1625 | 4.43 / 443 | 72.7 |
| 1 wt % aqueous solution of acid treated gelatin | — | 11.55 / 1155 | 5.40 / 540 | 53.2 | — | — | — |
| 0.1 wt % porcine collagen/5 mM acetic acid solution | — | 0.024 / 24 | 0.0013 / 1.3 | 94.6 | — | — | — |

EDA-MCC had a low anion exchange capacity that was about 1/1.3 that of the polylysine-carrying spherical cellulose but had a high LPS adsorption rate that was about 1.1 times that of the polylysine-carrying spherical cellulose. TMDH-MCC had a low anion exchange capacity that was about 1/1.7 that of the polylysine-carrying spherical cellulose but had a high LPS adsorption rate that was about 1.1 to 1.8 or more times that of the polylysine-carrying spherical cellulose. Arg-MCC had a low anion exchange capacity that was about 1/1.9 that of the polylysine-carrying spherical cellulose but had a high LPS adsorption rate that was about 1.1 to 1.3 times that of the polylysine-carrying spherical cellulose.

Each of the above materials containing ET to be removed is a highly viscous material, and in particular, the aqueous pullulan solution is a material containing pullulan at a high concentration of 10 wt %. The gelatin and the collagen have an amino group as a cationic group. The ET adsorbent of the present invention has been revealed to have high ET removability for materials having cationic groups and for highly viscous materials.

(4) Study for Preparing Column

The Arg-MCC prepared in Example 6 was used to prepare a column. In other words, the Arg-MCC was dried under reduced pressure at room temperature for 24 hours, and 490 to 670 mg of the dried material was placed in a column container having a volume of about 1 ml.

Water was allowed to pass at a flow rate of 0.5 to 4.0 mL/min, and the load pressure was measured. The load pressure was measured 5 minutes after flow start only in the case of a water flow rate of 0.5 mL/min and was measured 1 minute after flow start in the other cases. The results are shown in Table 2. The unit of the load pressure in Table 2 is kg/cm$^2$.

TABLE 2

| Water flow (ml/min) | ET adsorbent packing amount (mg) | | | | | | |
|---|---|---|---|---|---|---|---|
| | 490 | 520 | 550 | 580 | 610 | 640 | 670 |
| 0.50 | 0 | 0 | 0 | 0 | 0 | 0 | 0 |
| 1.00 | 0 | 0 | 1 | 1 | 1 | 1 | 2 |
| 1.50 | 1 | 1 | 1 | 1 | 1 | 2 | 2 |
| 2.00 | 1 | 1 | 1 | 2 | 2 | 2 | 3 |
| 3.00 | 2 | 2 | 2 | 3 | 3 | 4 | 4 |
| 4.00 | 3 | 3 | 3 | 3 | 4 | 4 | 5 |

Through the column having a volume of about 1 ml, water was allowed to pass at a flow rate of 0.5 to 4.0 mL/min at a stable low pressure of 0 to 5 kg/cm$^2$. Problems including container breakage due to pressurization did not arise. The column packed with the ET adsorbent of the present invention has been revealed to be practically usable for ET removal from an aqueous composition.

INDUSTRIAL APPLICABILITY

The ET adsorbent of the present invention can sufficiently remove ET from a material containing ET to be removed and containing a substance having a cationic group and can efficiently remove ET from a highly viscous material. Therefore, the ET adsorbent is highly practical in the pharmaceutical product, food, and cosmetic fields.

The invention claimed is:

1. An endotoxin adsorbent consisting essentially of a crystalline cellulose having a nitrogen atom-containing cationic group, wherein the nitrogen atom-containing cationic group is introduced into hydroxy group(s) of the crystalline cellulose directly or through at least one activating agent selected from the group consisting of chloromethyloxirane, diglycidyl ether, epibromohydrin, ethylene glycol diglycidyl ether, p-toluenesulfonyl chloride, 2-fluoro-1-methylpyridinium, chloroacetyl chloride, hexamethylene diisocyanate, m-xylene diisocyanate, and toluene-2,4-diisocyanate.

2. The endotoxin adsorbent according to claim 1, wherein the nitrogen atom-containing cationic group is a functional group derived from a polyvalent amine and/or a quaternary ammonium group.

3. The endotoxin adsorbent according to claim 1, wherein the crystalline cellulose having a nitrogen atom-containing cationic group comprises the nitrogen atom-containing cationic group at a content of 0.05 to 3 meq/dry·g in terms of anion exchange capacity.

4. A column for removing endotoxin, the column comprising the endotoxin adsorbent according to claim 1 therein.

5. A method of removing endotoxin, the method comprising a step of bringing the endotoxin adsorbent according to claim 1 into contact with a material containing endotoxin to be removed.

6. A method of producing a material from which endotoxin has been removed, the method comprising a step of bringing the endotoxin adsorbent according to claim 1 into contact with a material containing endotoxin to be removed.

7. The endotoxin adsorbent according to claim 2, wherein the crystalline cellulose having a nitrogen atom-containing cationic group comprises the nitrogen atom-containing cationic group at a content of 0.05 to 3 meq/dry·g in terms of anion exchange capacity.

8. A column for removing endotoxin, the column comprising the endotoxin adsorbent according to claim 2 therein.

9. A column for removing endotoxin, the column comprising the endotoxin adsorbent according to claim 3 therein.

10. A method of removing endotoxin, the method comprising a step of bringing the endotoxin adsorbent according to claim 2 into contact with a material containing endotoxin to be removed.

11. A method of removing endotoxin, the method comprising a step of bringing the endotoxin adsorbent according to claim 3 into contact with a material containing endotoxin to be removed.

12. A method of producing a material from which endotoxin has been removed, the method comprising a step of bringing the endotoxin adsorbent according to claim 2 into contact with a material containing endotoxin to be removed.

13. A method of producing a material from which endotoxin has been removed, the method comprising a step of bringing the endotoxin adsorbent according to claim 3 into contact with a material containing endotoxin to be removed.

* * * * *